United States Patent
Flournoy et al.

(10) Patent No.: US 6,180,403 B1
(45) Date of Patent: Jan. 30, 2001

(54) ANTISENSE INHIBITION OF TUMOR NECROSIS FACTOR ALPHA CONVERTING ENZYME (TACE) EXPRESSION

(75) Inventors: Shin Cheng Flournoy, San Diego; C. Frank Bennett, Carlsbad, both of CA (US)

(73) Assignee: Isis Pharmaceuticals Inc., Carlsbad, CA (US)

( * ) Notice: Under 35 U.S.C. 154(b), the term of this patent shall be extended for 0 days.

(21) Appl. No.: 09/429,093

(22) Filed: Oct. 28, 1999

(51) Int. Cl.$^7$ .................... C07H 21/04; C12N 15/00; C12Q 1/68
(52) U.S. Cl. .................. 435/375; 435/366; 435/6; 435/91.1; 435/325; 536/23.1; 536/24.31; 536/24.33; 536/24.5
(58) Field of Search .................... 435/6, 91.1, 91.3, 435/375, 325; 536/23.1, 23.2, 24.5, 24.3, 24.33, 24.31; 514/44

(56) References Cited

U.S. PATENT DOCUMENTS

| | | | |
|---|---|---|---|
| 5,484,699 | * 1/1996 | Bouma et al. | 435/5 |
| 5,563,037 | * 10/1996 | Sutherland et al. | 435/6 |
| 5,629,285 | 5/1997 | Black et al. | 514/2 |
| 5,693,532 | * 12/1997 | McSwiggen et al. | 435/366 |
| 5,801,154 | * 1/1996 | Baracchini et al. | 514/44 |

FOREIGN PATENT DOCUMENTS

WO93/25563 * 12/1993 (WO) .
WO97/35538 * 12/1993 (WO) .
WO 96/41624    12/1996 (WO) .

OTHER PUBLICATIONS

Eigler, A., et al., "Taming TNF:strategies to restrain this proinflammatory cytokine", *Immunol. Today* 1997 18, 487–492.
Kumar, V., et al., "An Essential Role for Ectodomain Shedding in Mammalian Development", *Cell Biol Int.* 1995 19, 373–388.
Peschon, J.J., et al., "Transforming Growth Factor Alpha", *Science* 1998 282, 1281–1284.
Agrawal, TIBTech, vol. 14, p. 376–387, Oct. 1996.*
Branch, TIBS 23, p. 45–50, Feb. 1998.*
James, Antiviral Chemistry and Chemotherapy, 2(4), p. 191–214, 1991.*
Milner et al. Nature Biotechnology, vol. 15, p. 537–541, Jun. 1997.*
Crooke, "Antisense Research and Application", Springer, New York, p. 1–50, Oct. 1996.*

* cited by examiner

Primary Examiner—Remy Yucel
Assistant Examiner—Karen A Lacourciere
(74) Attorney, Agent, or Firm—Law Offices of Jane Massey Licata

(57) ABSTRACT

Compositions and methods are provided for inhibiting the expression of human tumor necrosis factor-α-converting enzyme (TACE). Antisense oligonucleotides targeted to nucleic acids encoding TACE are preferred. Methods of using these oligonucleotides for inhibition of TACE expression and for treatment of diseases, particularly inflammatory and autoimmune diseases, associated with overexpression of TACE or TNF-α are provided.

14 Claims, No Drawings

SEQUENCE LISTING

<160> NUMBER OF SEQ ID NOS: 18

<210> SEQ ID NO 1
<211> LENGTH: 3014
<212> TYPE: DNA
<213> ORGANISM: Homo sapiens
<220> FEATURE:
<221> NAME/KEY: CDS
<222> LOCATION: (115)..(2589)
<300> PUBLICATION INFORMATION:
<303> JOURNAL: Nature
<304> VOLUME: 385
<305> ISSUE: 6618
<306> PAGES: 729-733
<307> DATE: 1997-02-20
<308> DATABASE ACCESSION NUMBER: U69611/Genbank
<309> DATABASE ENTRY DATE: 1997-04-09

<400> SEQUENCE: 1

```
ggattgaggg gctaggccgg gcggatcccg tcctcccccg atgtgagcag ttttccgaaa         60
ccccgtcagg cgaaggctgc ccagagaggt ggagtcggta gcggggccgg gaac atg        117
                                                             Met
                                                               1 agg cag tct ctc cta ttc ctg acc agc gtg gtt cct ttc gtg ctg gcg        165
Arg Gln Ser Leu Leu Phe Leu Thr Ser Val Val Pro Phe Val Leu Ala
              5                  10                  15 ccg cga cct ccg gat gac ccg ggc ttc ggc ccc cac cag aga ctc gag        213
Pro Arg Pro Pro Asp Asp Pro Gly Phe Gly Pro His Gln Arg Leu Glu
         20                  25                  30 aag ctt gat tct ttg ctc tca gac tac gat att ctc tct tta tct aat        261
Lys Leu Asp Ser Leu Leu Ser Asp Tyr Asp Ile Leu Ser Leu Ser Asn
     35                  40                  45 atc cag cag cat tcg gta aga aaa aga gat cta cag act tca aca cat        309
Ile Gln Gln His Ser Val Arg Lys Arg Asp Leu Gln Thr Ser Thr His
 50                  55                  60                  65 gta gaa aca cta cta act ttt tca gct ttg aaa agg cat ttt aaa tta        357
Val Glu Thr Leu Leu Thr Phe Ser Ala Leu Lys Arg His Phe Lys Leu
                 70                  75                  80 tac ctg aca tca agt act gaa cgt ttt tca caa aat ttc aag gtc gtg        405
Tyr Leu Thr Ser Ser Thr Glu Arg Phe Ser Gln Asn Phe Lys Val Val
             85                  90                  95 gtg gtg gat ggt aaa aac gaa agc gag tac act gta aaa tgg cag gac        453
Val Val Asp Gly Lys Asn Glu Ser Glu Tyr Thr Val Lys Trp Gln Asp
        100                 105                 110 ttc ttc act gga cac gtg gtt ggt gag cct gac tct agg gtt cta gcc        501
Phe Phe Thr Gly His Val Val Gly Glu Pro Asp Ser Arg Val Leu Ala
    115                 120                 125 cac ata aga gat gat gat gtt ata atc aga atc aac aca gat ggg gcc        549
His Ile Arg Asp Asp Asp Val Ile Ile Arg Ile Asn Thr Asp Gly Ala
130                 135                 140                 145 gaa tat aac ata gag cca ctt tgg aga ttt gtt aat gat acc aaa gac        597
Glu Tyr Asn Ile Glu Pro Leu Trp Arg Phe Val Asn Asp Thr Lys Asp
                150                 155                 160 aaa aga atg tta gtt tat aaa tct gaa gat atc aag aat gtt tca cgt        645
Lys Arg Met Leu Val Tyr Lys Ser Glu Asp Ile Lys Asn Val Ser Arg
            165                 170                 175 ttg cag tct cca aaa gtg tgt ggt tat tta aaa gtg gat aat gaa gag        693
Leu Gln Ser Pro Lys Val Cys Gly Tyr Leu Lys Val Asp Asn Glu Glu
        180                 185                 190 ttg ctc cca aaa ggg tta gta gac aga gaa cca cct gaa gag ctt gtt        741
Leu Leu Pro Lys Gly Leu Val Asp Arg Glu Pro Pro Glu Glu Leu Val
```

```
                195                 200                 205
cat cga gtg aaa aga aga gct gac cca gat ccc atg aag aac acg tgt        789
His Arg Val Lys Arg Arg Ala Asp Pro Asp Pro Met Lys Asn Thr Cys
210                 215                 220                 225 aaa tta ttg gtg gta gca gat cat cgc ttc tac aga tac atg ggc aga        837
Lys Leu Leu Val Val Ala Asp His Arg Phe Tyr Arg Tyr Met Gly Arg
                230                 235                 240 ggg gaa gag agt aca act aca aat tac tta ata gag cta att gac aga        885
Gly Glu Glu Ser Thr Thr Thr Asn Tyr Leu Ile Glu Leu Ile Asp Arg
            245                 250                 255 gtt gat gac atc tat cgg aac act tca tgg gat aat gca ggt ttt aaa        933
Val Asp Asp Ile Tyr Arg Asn Thr Ser Trp Asp Asn Ala Gly Phe Lys
        260                 265                 270 ggc tat gga ata cag ata gag cag att cgc att ctc aag tct cca caa        981
Gly Tyr Gly Ile Gln Ile Glu Gln Ile Arg Ile Leu Lys Ser Pro Gln
    275                 280                 285 gag gta aaa cct ggt gaa aag cac tac aac atg gca aaa agt tac cca       1029
Glu Val Lys Pro Gly Glu Lys His Tyr Asn Met Ala Lys Ser Tyr Pro
290                 295                 300                 305 aat gaa gaa aag gat gct tgg gat gtg aag atg ttg cta gag caa ttt       1077
Asn Glu Glu Lys Asp Ala Trp Asp Val Lys Met Leu Leu Glu Gln Phe
                310                 315                 320 agc ttt gat ata gct gag gaa gca tct aaa gtt tgc ttg gca cac ctt       1125
Ser Phe Asp Ile Ala Glu Glu Ala Ser Lys Val Cys Leu Ala His Leu
            325                 330                 335 ttc aca tac caa gat ttt gat atg gga act ctt gga tta gct tat gtt       1173
Phe Thr Tyr Gln Asp Phe Asp Met Gly Thr Leu Gly Leu Ala Tyr Val
        340                 345                 350 ggc tct ccc aga gca aac agc cat gga ggt gtt tgt cca aag gct tat       1221
Gly Ser Pro Arg Ala Asn Ser His Gly Gly Val Cys Pro Lys Ala Tyr
    355                 360                 365 tat agc cca gtt ggg aag aaa aat atc tat ttg aat agt ggt ttg acg       1269
Tyr Ser Pro Val Gly Lys Lys Asn Ile Tyr Leu Asn Ser Gly Leu Thr
370                 375                 380                 385 agc aca aag aat tat ggt aaa acc atc ctt aca aag gaa gct gac ctg       1317
Ser Thr Lys Asn Tyr Gly Lys Thr Ile Leu Thr Lys Glu Ala Asp Leu
                390                 395                 400 gtt aca act cat gaa ttg gga cat aat ttt gga gca gaa cat gat ccg       1365
Val Thr Thr His Glu Leu Gly His Asn Phe Gly Ala Glu His Asp Pro
            405                 410                 415 gat ggt cta gca gaa tgt gcc ccg aat gag gac cag gga ggg aaa tat       1413
Asp Gly Leu Ala Glu Cys Ala Pro Asn Glu Asp Gln Gly Gly Lys Tyr
        420                 425                 430 gtc atg tat ccc ata gct gtg agt ggc gat cac gag aac aat aag atg       1461
Val Met Tyr Pro Ile Ala Val Ser Gly Asp His Glu Asn Asn Lys Met
    435                 440                 445 ttt tca aac tgc agt aaa caa tca atc tat aag acc att gaa agt aag       1509
Phe Ser Asn Cys Ser Lys Gln Ser Ile Tyr Lys Thr Ile Glu Ser Lys
450                 455                 460                 465 gcc cag gag tgt ttt caa gaa cgc agc aat aaa gtt tgt ggg aac tcg       1557
Ala Gln Glu Cys Phe Gln Glu Arg Ser Asn Lys Val Cys Gly Asn Ser
                470                 475                 480 agg gtg gat gaa gga gaa gag tgt gat cct ggc atc atg tat ctg aac       1605
Arg Val Asp Glu Gly Glu Glu Cys Asp Pro Gly Ile Met Tyr Leu Asn
            485                 490                 495 aac gac acc tgc tgc aac agc gac tgc acg ttg aag gaa ggt gtc cag       1653
Asn Asp Thr Cys Cys Asn Ser Asp Cys Thr Leu Lys Glu Gly Val Gln
        500                 505                 510 tgc agt gac agg aac agt cct tgc tgt aaa aac tgt cag ttt gag act       1701
```

```
                                                          -continued

Cys Ser Asp Arg Asn Ser Pro Cys Cys Lys Asn Cys Gln Phe Glu Thr
515                 520                 525 gcc cag aag aag tgc cag gag gcg att aat gct act tgc aaa ggc gtg     1749
Ala Gln Lys Lys Cys Gln Glu Ala Ile Asn Ala Thr Cys Lys Gly Val
530                 535                 540                 545 tcc tac tgc aca ggt aat agc agt gag tgc ccg cct cca gga aat gct     1797
Ser Tyr Cys Thr Gly Asn Ser Ser Glu Cys Pro Pro Pro Gly Asn Ala
                550                 555                 560 gaa gat gac act gtt tgc ttg gat ctt ggc aag tgt aag gat ggg aaa     1845
Glu Asp Asp Thr Val Cys Leu Asp Leu Gly Lys Cys Lys Asp Gly Lys
            565                 570                 575 tgc atc cct ttc tgc gag agg gaa cag cag ctg gag tcc tgt gca tgt     1893
Cys Ile Pro Phe Cys Glu Arg Glu Gln Gln Leu Glu Ser Cys Ala Cys
        580                 585                 590 aat gaa act gac aac tcc tgc aag gtg tgc tgc agg gac ctt tcc ggc     1941
Asn Glu Thr Asp Asn Ser Cys Lys Val Cys Cys Arg Asp Leu Ser Gly
    595                 600                 605 cgc tgt gtg ccc tat gtc gat gct gaa caa aag aac tta ttt ttg agg     1989
Arg Cys Val Pro Tyr Val Asp Ala Glu Gln Lys Asn Leu Phe Leu Arg
610                 615                 620                 625 aaa gga aag ccc tgt aca gta gga ttt tgt gac atg aat ggc aaa tgt     2037
Lys Gly Lys Pro Cys Thr Val Gly Phe Cys Asp Met Asn Gly Lys Cys
                630                 635                 640 gag aaa cga gta cag gat gta att gaa cga ttt tgg gat ttc att gac     2085
Glu Lys Arg Val Gln Asp Val Ile Glu Arg Phe Trp Asp Phe Ile Asp
            645                 650                 655 cag ctg agc atc aat act ttt gga aag ttt tta gca gac aac atc gtt     2133
Gln Leu Ser Ile Asn Thr Phe Gly Lys Phe Leu Ala Asp Asn Ile Val
        660                 665                 670 ggg tct gtc ctg gtt ttc tcc ttg ata ttt tgg att cct ttc agc att     2181
Gly Ser Val Leu Val Phe Ser Leu Ile Phe Trp Ile Pro Phe Ser Ile
    675                 680                 685 ctt gtc cat tgt gtg gat aag aaa ttg gat aaa cag tat gaa tct ctg     2229
Leu Val His Cys Val Asp Lys Lys Leu Asp Lys Gln Tyr Glu Ser Leu
690                 695                 700                 705 tct ctg ttt cac ccc agt aac gtc gaa atg ctg agc agc atg gat tct     2277
Ser Leu Phe His Pro Ser Asn Val Glu Met Leu Ser Ser Met Asp Ser
                710                 715                 720 gca tcg gtt cgc att atc aaa ccc ttt cct gcg ccc cag act cca ggc     2325
Ala Ser Val Arg Ile Ile Lys Pro Phe Pro Ala Pro Gln Thr Pro Gly
            725                 730                 735 cgc ctg cag cct gcc cct gtg atc cct tcg gcg cca gca gct cca aaa     2373
Arg Leu Gln Pro Ala Pro Val Ile Pro Ser Ala Pro Ala Ala Pro Lys
        740                 745                 750 ctg gac cac cag aga atg gac acc atc cag gaa gac ccc agc aca gac     2421
Leu Asp His Gln Arg Met Asp Thr Ile Gln Glu Asp Pro Ser Thr Asp
    755                 760                 765 tca cat atg gac gag gat ggg ttt gag aag gac ccc ttc cca aat agc     2469
Ser His Met Asp Glu Asp Gly Phe Glu Lys Asp Pro Phe Pro Asn Ser
770                 775                 780                 785 agc aca gct gcc aag tca ttt gag gat ctc acg gac cat ccg gtc acc     2517
Ser Thr Ala Ala Lys Ser Phe Glu Asp Leu Thr Asp His Pro Val Thr
                790                 795                 800 aga agt gaa aag gct gcc tcc ttt aaa ctg cag cgt cag aat cgt gtt     2565
Arg Ser Glu Lys Ala Ala Ser Phe Lys Leu Gln Arg Gln Asn Arg Val
            805                 810                 815 gac agc aaa gaa aca gag tgc taa tttagttctc agctcttctg acttaagtgt   2619
Asp Ser Lys Glu Thr Glu Cys
        820                 825
```

-continued

```
gcaaaatatt tttatagatt tgacctacaa tcaatcacag cttatatttt gtgaagactg    2679
ggaagtgact tagcagatgc tggtcatgtg tttgaacttc ctgcaggtaa acagttcttg    2739
tgtggtttgg cccttctcct tttgaaaagg taaggtgaag gtgaatctag cttattttga    2799
ggctttcagg ttttagtttt taaaatatct tttgacctgt ggtgcaaaag cagaaaatac    2859
agctggattg ggttatgagt atttacgttt ttgtaaatta atcttttata ttgataacag    2919
cactgactag ggaaatgatc agtttttttt ttatacactg taatgaaccg ctgaatatga    2979
ggcatttggc atttatttgt gatgacaact ggaat                               3014

<210> SEQ ID NO 2
<211> LENGTH: 20
<212> TYPE: DNA
<213> ORGANISM: Artificial Sequence
<220> FEATURE:
<223> OTHER INFORMATION: antisense sequence

<400> SEQUENCE: 2
cctagtcagt gctgttatca                                                20

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
gctgtgattg attgtaggtc                                                20

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
agcatctgct aagtcacttc                                                20

<210> SEQ ID NO 5
<211> LENGTH: 20
<212> TYPE: DNA
<213> ORGANISM: Artificial Sequence
<220> FEATURE:
<223> OTHER INFORMATION: antisense sequence

<400> SEQUENCE: 5
agctgagaac taaattagca                                                20

<210> SEQ ID NO 6
<211> LENGTH: 20
<212> TYPE: DNA
<213> ORGANISM: Artificial Sequence
<220> FEATURE:
<223> OTHER INFORMATION: antisense sequence

<400> SEQUENCE: 6
tgagaactaa attagcactc                                                20

<210> SEQ ID NO 7
<211> LENGTH: 20
<212> TYPE: DNA
<213> ORGANISM: Artificial Sequence
```

```
<220> FEATURE:
<223> OTHER INFORMATION: antisense sequence

<400> SEQUENCE: 7
ttagcactct gtttctttgc                                                    20

<210> SEQ ID NO 8
<211> LENGTH: 20
<212> TYPE: DNA
<213> ORGANISM: Artificial Sequence
<220> FEATURE:
<223> OTHER INFORMATION: antisense sequence

<400> SEQUENCE: 8
ctgcagttta aaggaggcag                                                    20

<210> SEQ ID NO 9
<211> LENGTH: 20
<212> TYPE: DNA
<213> ORGANISM: Artificial Sequence
<220> FEATURE:
<223> OTHER INFORMATION: antisense sequence

<400> SEQUENCE: 9
ctgtcaacac gattctgacg                                                    20

<210> SEQ ID NO 10
<211> LENGTH: 20
<212> TYPE: DNA
<213> ORGANISM: Artificial Sequence
<220> FEATURE:
<223> OTHER INFORMATION: antisense sequence

<400> SEQUENCE: 10
aaatgacttg gcagctgtgc                                                    20

<210> SEQ ID NO 11
<211> LENGTH: 20
<212> TYPE: DNA
<213> ORGANISM: Artificial Sequence
<220> FEATURE:
<223> OTHER INFORMATION: antisense sequence

<400> SEQUENCE: 11
aaccacgctg gtcaggaata                                                    20

<210> SEQ ID NO 12
<211> LENGTH: 20
<212> TYPE: DNA
<213> ORGANISM: Artificial Sequence
<220> FEATURE:
<223> OTHER INFORMATION: antisense sequence

<400> SEQUENCE: 12
ataggagaga ctgcctcatg                                                    20

<210> SEQ ID NO 13
<211> LENGTH: 20
<212> TYPE: DNA
<213> ORGANISM: Artificial Sequence
<220> FEATURE:
<223> OTHER INFORMATION: control sequence

<400> SEQUENCE: 13
cctagtatgt gctgctatca                                                    20
```

```
<210> SEQ ID NO 14
<211> LENGTH: 20
<212> TYPE: DNA
<213> ORGANISM: Artificial Sequence
<220> FEATURE:
<223> OTHER INFORMATION: control sequence

<400> SEQUENCE: 14
ggatgttcgt cctcctcaca                                                    20

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
gtgtcctact gcacaggtaa tagc                                               24

<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
aatgacttgg cagctgtgct gct                                                23

<210> SEQ ID NO 17
<211> LENGTH: 11
<212> TYPE: PRT
<213> ORGANISM: Artificial Sequence
<220> FEATURE:
<223> OTHER INFORMATION: Peptide fragment

<400> SEQUENCE: 17

Arg Ala Asp Pro Asp Pro Met Lys Asn Thr Cys
 1               5                  10

<210> SEQ ID NO 18
<211> LENGTH: 20
<212> TYPE: DNA
<213> ORGANISM: Artificial Sequence
<220> FEATURE:
<223> OTHER INFORMATION: control antisense sequence

<400> SEQUENCE: 18
ggatgttcgt cctcctcaca                                                    20
```

ANTISENSE INHIBITION OF TUMOR NECROSIS FACTOR ALPHA CONVERTING ENZYME (TACE) EXPRESSION

FIELD OF THE INVENTION

This invention relates to compositions and methods for modulating expression of the human TNF-α-converting enzyme (TACE) gene, which encodes a disintegrin metalloprotease involved in the processing of tumor necrosis factor a (TNF-α), a cytokine implicated in infectious and inflammatory disease. This invention is also directed to methods for inhibiting TACE processing of TNF-α; these methods can be used diagnostically or therapeutically. Furthermore, this invention is directed to modulation of TNF-α mediated cellular events, especially shedding of L-selectin, and also to treatment of conditions associated with the overexpression of the mature, processed form of the TNF-α molecule.

BACKGROUND OF THE INVENTION

Tumor necrosis factor a (TNF-α, also cachectin) is an important cytokine that plays a role in host defense. The cytokine is produced primarily in macrophages and monocytes in response to infection, invasion, injury, or inflammation. Some examples of inducers of TNF-α include bacterial endotoxins, bacteria, viruses, lipopolysaccharide (LPS) and cytokines including GM-CSF, IL-1, Il-2 and IFN-γ.

TNF-α is initially synthesized as a 26 kD membrane-bound protein. A 17 kD fragment of TNF-α is secreted and forms a trimer with other secreted forms. This trimer interacts with two different receptors, TNF receptor I (TNFRI, p55) and TNFRII (p75), in order to transduce its effects—the net result of which is altered gene expression and/or apoptosis. Cellular factors induced by TNF-α include interleukin-1 (IL-1), interleukin-6 (IL-6), interleukin-8 (IL-8), interferon-γ (IFN-γ), platelet derived growth factor (PDGF), epidermal growth factor (EGF), and endothelial cell adhesion molecules including endothelial leukocyte adhesion molecule 1 (ELAM-1), intercellular adhesion molecule-1 (ICAM-1) and vascular cell adhesion molecule-1 (VCAM-1) (Tracey, K. J., et al., *Annu. Rev. Cell Biol.*, 1993, 9, 317–343; Arvin, B., et al., *Ann. NY Acad. Sci.*, 1995, 765, 62–71).

The processing of TNF-α from its membrane-bound form to its secreted form is due to a specific metalloprotease known as TNF-α converting enzyme (TACE, also ADAM17). TACE is a member of the ADAM (A Disintegrin And Metalloprotease) family. TACE has also been shown to have a direct proteolytic role in the processing of other membrane proteins including p75 TNF receptor, L-selectin and transforming growth factor-α (TGF-α; Peschon, J. J., et al., Science, 1998, 282, 1281–1284). L-selectin, in particular, is an adhesion molecule involved in leukocyte rolling and mediates the attachment of leukocytes to endothelium at sites of inflammation as well as the binding of lymphocytes to high endothelial venules of peripheral lymph nodes.

Inhibitors of TACE will inhibit release of TNF-α into the extracellular environment, preventing TNF-α mediated signaling. Thus, TACE inhibitors may have clinical utility in diseases associated with the over-production of TNF-α. Additional utility may be present in regulating the processing of other membrane-bound TACE substrates, such as TGF-α, which has been shown to be involved in many cancers and psoriasis (Kumar, V., et al., *Cell Biol Int.*, 1995, 19, 373–388) and the β-amyloid precursor protein.

Overexpression of TNF-α often results in disease states, particularly in infectious, inflammatory and autoimmune diseases. This process may involve the apoptotic pathways (Ksontini, R., et al., *J. Immunol.*, 1998, 160, 4082–4089). High levels of plasma TNF-α have been found in infectious diseases such as sepsis syndrome, bacterial meningitis, cerebral malaria, and AIDS; autoimmune diseases such as rheumatoid arthritis, inflammatory bowel disease (including Crohn's disease), sarcoidosis, multiple sclerosis, Kawasaki syndrome, graft-versus-host disease and transplant (allograft) rejection; organ failure conditions such as adult respiratory distress syndrome, congestive heart failure, acute liver failure and myocardial infarction (Eigler, A., et al., *Immunol. Today*, 1997, 18, 487–492). Other diseases in which TNF-α is involved include asthma (Shah, A., et al., *Clinical and Experimental Allergy*, 1995, 25, 1038–1044), brain injury following ischemia (Arvin, B., et al., *Ann. NY Acad. Sci.*, 1995, 765, 62–71), non-insulin-dependent diabetes mellitus (Hotamisligil, G. S., et al., *Science*, 1993, 259, 87–90), insulin-dependent diabetes mellitus (Yang, X.-D., et al., *J. Exp. Med.*, 1994, 180, 995–1004), hepatitis (Ksontini, R., et al., *J. Immunol.*, 1998, 160, 4082–4089), atopic dermatitis (Sumimoto, S., et al., *Arch. Dis. Child.*, 1992, 67, 277–279), and pancreatitis (Norman, J. G., et al., *Surgery*, 1996, 120, 515–521). Further, Suganuma, M., et al. (*Cancer Res.*, 1996, 56, 3711–3715) suggest that inhibitors of TNF-α may be useful for cancer prevention. In addition, elevated TNF-α expression may play a role in obesity (Kern, P. A., *J. Nutr.*, 1997, 127, 1917S–1922S). TNF-α was found to be expressed in human adipocytes and increased expression, in general, correlated with obesity.

L-selectin has been found to be involved in ischemia/reperfusion injury, especially myocardial (Ma, X.L., et al., *Circulation*, 1993, 88, 649–658), and liver (Yadav, S. S., *Am. J. Physiol.*, 1998, 275, G1341–G1352) and thromboembolic stroke (Bednar, M. M., et al., *Neurol. Res.*, 1998, 20, 403–408); acute myeloid leukemia (Extermann, M., et al., *Blood*, 1998, 92, 3115–3122), B-cell chronic lymphocytic leukemia (Csanaky, G., et al., *Haematologica*, 1994, 79, 132–136); experimental autoimmune encephalomyelitis (EAE), an animal model of multiple sclerosis (Archelos, J. J., et al., *J. Neurol. Sci.*, 1998, 159, 127–134), human T-cell lymphotropic virus type I-associated myelopathy (Tsujino, A., et al., *J. Neurol. Sci.*, 1998, 155, 76–79), meningoencephalitis (Buhrer, C., et al., *Arch. Dis. Child.*, 1996, 74, 288–292); rheumatoid arthritis (Kurohori, Y., et al., *Clin. Rheumatol.*, 1995, 14, 335–341), ulcerative colitis (Seidelin, J. B., et al., *Am. J. Gastroenterol.*, 1998, 93, 1854–1859); chronic lung disease (Kotecha, S., et al., *Arch. Dis. Child. Fetal Neonatal Ed.*, 1998, 78, F143–F147).

There are currently several approaches to inhibiting TNF-α expression. Approaches used to treat rheumatoid arthritis include a chimeric anti-TNF-α antibody, a humanized monoclonal anti-TNF-α antibody, and recombinant human soluble TNF-α receptor (Camussi, G., *Drugs*, 1998, 55, 613–620). Other examples are indirect TNF-α inhibitors including phosphodiesterase inhibitors (e.g. pentoxifylline) and metalloprotease inhibitors (Eigler, A., et al., *Immunol. Today*, 1997, 18, 487–492). An additional class of a direct TNF-α inhibitor is oligonucleotides, including triplex-forming oligonucleotides, ribozymes, and antisense oligonucleotides.

Inhibitors of L-selectin include monoclonal antibodies (Bednar, M. M., et al., *Neurol. Res.*, 1998, 20, 403–408), fucoidin (Nasu, T., et al., *Immunol. Lett.*, 1997, 59, 47–51), and oligonucleotide aptamers (Ringquist, S. and Parma, D., *Cytometry*, 1998, 33, 394–405).

Although broad spectrum inhibitors of matrix metalloproteases are effective in inhibiting TACE, specific inhibitors are desired for clinical use.

U.S. Pat. No. 5,629,285 describes small molecule inhibitors of TACE based on peptidyl derivatives. WO 96/41624 describes the use of antisense oligonucleotides to block expression of TACE, but no oligonucleotide sequences were disclosed.

There remains an unmet need for therapeutic compositions and methods targeting expression of TACE, and disease processes associated therewith.

SUMMARY OF THE INVENTION

The present invention provides oligonucleotides which are targeted to nucleic acids encoding TACE and are capable of modulating TACE expression. The present invention also provides chimeric oligonucleotides targeted to nucleic acids encoding human TACE. The oligonucleotides of the invention are believed to be useful both diagnostically and therapeutically, and are believed to be particularly useful in the methods of the present invention.

The present invention also comprises methods of modulating the expression of human TACE, in cells and tissues, using the oligonucleotides of the invention. Methods of inhibiting TACE expression are provided; these methods are believed to be useful both therapeutically and diagnostically. These methods are also useful as tools, for example, for detecting and determining the role of TACE in various cell functions and physiological processes and conditions and for diagnosing conditions associated with expression of TACE or its substrate, TNF-α.

The present invention also comprises methods for diagnosing and treating infectious and inflammatory diseases, particularly diabetes, rheumatoid arthritis, Crohn's disease, pancreatitis, multiple sclerosis, atopic dermatitis and hepatitis. These methods are believed to be useful, for example, in diagnosing TACE- or TNF-α-associated disease progression. These methods employ the oligonucleotides of the invention. These methods are believed to be useful both therapeutically, including prophylactically, and as clinical research and diagnostic tools.

The present invention further comprises methods of inhibiting shedding of L-selectin and diseases and conditions associated with altered L-selectin shedding.

DETAILED DESCRIPTION OF THE INVENTION

TNF-α plays an important regulatory role in the immune response to various foreign agents. Overexpression of TNF-α results in a number of infectious and inflammatory diseases. As such, this cytokine represents an attractive target for treatment of such diseases. In particular, modulation of the expression of TNF-α may be useful for the treatment of diseases such as Crohn's disease, diabetes mellitus, multiple sclerosis, rheumatoid arthritis, hepatitis, pancreatitis and asthma.

TACE is responsible for processing the membrane-bound form of TNF-α into its secreted form. Thus, modulation of TACE is thought to an effective means of modulating TNF-α processing and diseases or conditions associated with expression of TNF-α.

As disclosed herein, TACE is also responsible for the shedding of L-selectin. Modulation of TACE may also be an effective means of modulating L-selectin and diseases or conditions associated with L-selectin.

The present invention employs antisense compounds, particularly oligonucleotides, for use in modulating the function of nucleic acid molecules encoding TACE, ultimately modulating the amount of TACE produced and the amount of processed TNF-α. This is accomplished by providing oligonucleotides which specifically hybridize with nucleic acids, preferably mRNA, encoding TACE.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding TACE; in other words, a gene encoding TACE, or mRNA expressed from the TACE gene. mRNA which encodes TACE is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed MRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding TACE, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of TACE. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The oligonucleotides of this invention can be used in diagnostics, therapeutics, prophylaxis, and as research reagents and in kits. Since the oligonucleotides of this invention hybridize to nucleic acids encoding TACE, sandwich, calorimetric and other assays can easily be constructed to exploit this fact. Provision of means for detecting hybridization of oligonucleotide with the TACE gene or mRNA can routinely be accomplished. Such provision may include enzyme conjugation, radiolabelling or any other suitable detection systems. Kits for detecting the presence or absence of TACE may also be prepared.

The present invention is also suitable for diagnosing abnormal inflammatory states in tissue or other samples from patients suspected of having an inflammatory disease such as rheumatoid arthritis. The ability of the oligonucleotides of the present invention to inhibit inflammatory processes may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide (s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, and borano-phosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—,—$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S-, or N-alkyl, O-alkyl-O-alkyl, O-, S-, or N-alkenyl, or O—, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n$O$CH_3$, O($CH_2$)$_2$ON($CH_3$)$_2$, O($CH_2$)$_n$NH$_2$, O($CH_2$)$_n CH_3$, O($CH_2$)$_n$ONH$_2$ and O($CH_2$)$_n$ON[($CH_2$)$_n CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—CH$_2$CH$_2$OCH$_3$, also known as 2'—O—(2-methoxyethyl) or 2'-MOE) (Martin et al., *Helv. Chim. Acta* 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (2'-DMAEOE), i.e., 2'—O—CH$_2$—O—CH$_2$—N(CH$_2$)$_2$.

Other preferred modifications include 2'-methoxy (2'—O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. : 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N. Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O- hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH\ O_2CH)_3$ modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and. 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of hese broad categories may be included.

Various fatty acids and their derivatives which act as enetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)[Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor.

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, intradermal and transdermal), oral or parenteral. Parenteral administration includes intravenous drip, infusion or injection; subcutaneous, intraperitoneal or intramuscular injection; pulmonary administration, e.g., by inhalation or insufflation, or intracranial, e.g., intrathecal or intraventricular, administration, or administration into the cerebrospinal fluid. oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (*J. Med. Chem.* 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3', 5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3' phosphoramidites.

2'-(2-methoxyethyl)-modified amidites were synthesized according to Martin, P. (*Helv. Chim. Acta* 1995, 78, 486–506). For ease of synthesis, the last nucleotide may be a deoxynucleotide. 2'—O—CH$_2$CH$_2$OCH$_3$ cytosines may be 5-methyl cytosines.

Synthesis of 5-Methyl Cytosine Monomers:

2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxy-trityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/-Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyl-uridine

2'-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5"-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methyl-cytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et₃NH as the eluting solvent. The pure product fractions were evaporated to give 90 g (90%) of the title compound.

N⁴-Benzoyl-2'-O-methoxyethyl-5'-O-dimethoxytrityl-5-methylcytidine-3'-amidite N⁴-Benzoyl-2'-O-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxy-tetra-(isopropyl) phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-O-(Dimethylaminooxyethyl) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O²-2'-anhydro-5-methyluridine

O²-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O²-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-Butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy) ethyl]-5-methyluridine as white foam (1.95, 78%).

5'-O-tert-Butaldiphenylsilyl-2'-O-[N,N-dimethylaminooxdethyl]-5-methyluridine 5'-O-Tert-Butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temper ature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrof luoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling VA or ChemGenes, Needham Mass.

Oligonucleotides having methylene (methylimino) (MMI) backbones were synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Example 2
Human TACE Oligodeoxynucleotide Sequences

Antisense oligonucleotides were designed to target human TACE. Target sequence data are from the TACE CDNA sequence published by Black, R. A. et al. (*Nature,* 1997, 385, 729–733); Genbank accession number U69611, provided herein as SEQ ID NO: 1. Oligodeoxynucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 1. Oligonucleotide 14834 (SEQ ID NO. 14) is an antisense oligodeoxynucleotide targeted to the human tumor necrosis factor-α (TNF-α) and was used as a positive control.

The human Jurkat T cell line and the human promonocytic leukaemia cell line, THP-1 (American Type Culture Collection, Manassas, Va.) were maintained in RPMI 1640 growth media supplemented with 10% fetal calf serum (FCS; Life Technologies, Rockville, Md.). HUVEC cells (Clonetics, San Diego, Calif.) were cultivated in endothelial basal media supplemented with 10% fetal bovine serum (Hyclone, Logan, Utah).

NeoHK cells, human neonatal foreskin keratinocytes (obtained from Cascade Biologicals, Inc., Portland, Oreg.) were cultured in Keratinocyte Serum Free (SFM) medium containing the human recombinant Epidermal Growth Factor 1–53 and Bovine Pituitary Extract (Life Technologies, Rockville, Md.). For NeoHK cells, the cells were used between passages 2 to 6.

HUVEC and NeoHK cells were allowed to reach 75% confluency prior to use. The cells were washed twice with warm (37° C.) OPTI-MEM™ (Life Technologies). The cells were incubated in the presence of the appropriate culture medium, without the growth factors added, and the oligonucleotide formulated in LIPOFECTIN® (Life Technologies), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. For an initial screen, the oligonucleotide concentration was 300 nM in 10 µg/ml LIPOFECTIN®. Treatment was for four hours. After treatment, the medium was removed and the cells were further incubated in culture medium containing growth factors and 100 nM phorbol 12-myristate 13-acetate (PMA, Sigma, St. Louis, Mo.). mRNA was analyzed 4 hours post-induction with PMA. HUVEC cells were treated with 100 nM oligonucleotide in 10 µg/ml LIPOFECTIN®. HUVEC cells were not induced, but allowed to rest in normal growth media for 4 hours.

Jurkat and THP-1 cells were grown to approximately 75% confluency and resuspended in culture media at a density of $1 \times 10^7$ cells/ml. A total of $3.6 \times 10^6$ cells were employed for each treatment by combining 360 µl of cell suspension with oligonucleotide at the indicated concentrations to reach a final volume of 400 µl. Cells were then transferred to an electroporation cuvette and electroporated using an Electrocell Manipulator 600 instrument (Biotechnologies and Experimental Research, Inc.) employing 350 V, 100 µF, at 13 Ω. Electroporated cells were then transferred to conical tubes containing 5 ml of culture media, mixed by inversion, and plated onto 10 cm culture dishes.

Total mRNA was isolated using the RNEASY® Mini Kit (Qiagen, Valencia, Calif.; similar kits from other manufacturers may also be used), separated on a 1% agarose gel, transferred to HYBOND™-N+ membrane (Amersham Pharmacia Biotech, Piscataway, N.J.), a positively charged nylon membrane, and probed. A TACE probe was made using PCR amplification with the following primers: TS-1746 5'-GTGTCCTACTGCACAGGTAATAGC-3' SEQ ID NO. 15 BS-2489 5'-AATGACTTGGCAGCTGTGCTGCT-3' SEQ ID NO. 16 A glyceraldehyde 3-phosphate dehydrogenase (G3PDH) probe was purchased from Clontech (Palo Alto, Calif.), Catalog Number 9805-1. The fragments were purified from low-melting temperature agarose, as described in Maniatis, T., et al., *Molecular Cloning: A Laboratory Manual*, 1989 and labeled with REDIVUE™ $^{32}$P-dCTP (Amersham Pharmacia Biotech, Piscataway, N.J.) and Strip-EZ labelling kit (Ambion, Austin, Tex.). mRNA was quantitated by a PhosphoImager (Molecular Dynamics, Sunnyvale, Calif.).

Protein levels were measured using flow cytometry analysis. Following oligonucleotide treatment, cells were detached from the plates and analyzed for surface expression of cell adhesion molecules using a Becton Dickinson (San Jose, Calif.) FACScan. TACE anti-serum was prepared as described below. Human L-selectin (CD62L) monoclonal antibody and goat anti-mouse antibody were obtained from Becton Dickinson. TNF-α antibody was obtained from R & D Systems (Minneapolis, Minn.). Cell surface expression was calculated using the mean value of fluorescence intensity using 3,000–5,000 cells stained with the appropriate antibody for each sample and time point. Results are expressed as percentage of control (cell surface expression in cells that were not treated with oligonucleotides) based upon mean fluorescence intensity.

Preparation of TACE Anti-serum

An 11 mer peptide (R A D P D P M K N T C) (SEQ ID NO: 17) corresponding to the N-terminus of the human Tumor Necrosis Factor-Alpha Converting Enzyme (TACE) was synthesized. The peptide was reduced with the REDUCE-IMM™ Reducing kit (Pierce Chemical Company, rockford, Ill.) and coupled to IMJECT® maleimide-activated KLH (Pierce Chemical Company). This solution was allowed to react for two hours at room temperature and then dialyzed versus PBS.

Female NZW rabbits were chosen for production of polyclonal anti-serum. Preimmune serum was obtained just prior to immunization with TACEpep-KLH. Immunization was as follows: 500 µg TACEpep-KLH emulsified with an equal volume of TITERMAX™ adjuvant (Sigma Chemical Company, St. Louis, Mo.) was injected intradermally into approximately 10 sites along the rabbits back. The animals were boosted at weeks 3, 5 and 11 with an equal volume emulsion. Booster shots at weeks 3 and 5 contained 500 mg peptide and the boost at week 5 contained 250 mg. Serum samples were obtained at weeks 8, 12 and 15, with the week 15 bleed being a terminal bleed.

TABLE 1

Nucleotide Sequences of Chimeric (deoxy gapped) 2'-O-methoxyethyl Human TACE Antisense Oligonucleotides

| ISIS NO. | NUCLEOTIDE SEQUENCE[1] (5'→3') | SEQ ID NO: | TARGET GENE NUCLEOTIDE CO-ORDINATES[2] | GENE TARGET REGION |
|---|---|---|---|---|
| 16337 | CCTAGTCAGTGCTGTTATCA | 2 | 2911–2930 | 3'-UTR |
| 16338 | GCTGTGATTGATTGTAGGTC | 3 | 2641–2660 | 3'-UTR |
| 16339 | AGCATCTGCTAAGTCACTTC | 4 | 2681–2700 | 3'-UTR |
| 16340 | AGCTGAGAACTAAATTAGCA | 5 | 2584–2603 | stop |
| 16341 | TGAGAACTAAATTAGCACTC | 6 | 2581–2600 | stop |
| 16342 | TTAGCACTCTGTTTCTTTGC | 7 | 2570–2589 | stop |
| 16343 | CTGCAGTTTAAAGGAGGCAG | 8 | 2531–2550 | coding |
| 16344 | CTGTCAACACGATTCTGACG | 9 | 2551–2570 | coding |
| 16345 | AAATGACTTGGCAGCTGTGC | 10 | 2471–2490 | coding |
| 16346 | AACCACGCTGGTCAGGAATA | 11 | 0131–0150 | coding |
| 16347 | ATAGGAGAGACTGCCTCATG | 12 | 0114–0133 | AUG |
| 17965 | CCTAGTATGTGCTGCTATCA | 13 | mismatch control | |
| 14834 | GGATGTTCGTCCTCCTCACA | 14 | TNF-α control | |

TABLE 1-continued

Nucleotide Sequences of Chimeric (deoxy gapped)
2'-O-methoxyethyl Human TACE Antisense
Oligonucleotides

| ISIS NO. | NUCLEOTIDE SEQUENCE[1] (5'→3') | SEQ ID NO: | TARGET NUCLEOTIDE CO-ORDINATES[2] | GENE TARGET REGION |
|---|---|---|---|---|

[1]Emboldened residues are 2'-methoxyethoxy residues (others are 2'-deoxy-). All 2'-methoxyethoxy cytidines are 5-methyl-cytidines; all linkages are phosphorothioate linkages.
[2]Co-ordinates from Genbank Accession No. U69611, locus name "HSU69611", SEQ ID NO. 1.

Results for an initial screen in HUVEC cells are shown in Table 2. All oligonucleotides tested inhibited TACE mRNA expression greater than 70%.

TABLE 2

Inhibition of Human TACE mRNA Expression in HUVEC by Chimeric (2'-deoxy) Gapped Oligonucleotides

| ISIS No: | SEQ ID NO: | GENE TARGET REGION | % mRNA EXPRESSION | % mRNA INHIBITION |
|---|---|---|---|---|
| basal | — | — | 100.0% | — |
| 16337 | 2 | 3'-UTR | 13.8% | 86.2% |
| 16338 | 3 | 3'-UTR | 27.5% | 72.5% |
| 16339 | 4 | 3'-UTR | 22.1% | 77.9% |
| 16340 | 5 | stop | 18.2% | 81.8% |
| 16341 | 6 | stop | 11.8% | 88.2% |
| 16342 | 7 | stop | 15.9% | 84.1% |
| 16343 | 8 | coding | 20.1% | 79.9% |
| 16344 | 9 | coding | 13.0% | 87.0% |
| 16345 | 10 | coding | 10.4% | 89.6% |
| 16346 | 11 | coding | 18.4%. | 81.6% |
| 16347 | 12 | AUG | 23.7% | 76.3% |

Results for an initial screen in NeoHK cells are shown in Table 3. All oligonucleotides tested inhibited TACE mRNA expression greater than 55%.

TABLE 3

Inhibition of Human TACE mRNA Expression in NeoHK Cells by Chimeric (2'-deoxy) Gapped Oligonucleotides

| ISIS No: | SEQ ID NO: | GENE TARGET REGION | % mRNA EXPRESSION | % mRNA INHIBITION |
|---|---|---|---|---|
| basal | — | — | 100.0% | — |
| induced | — | — | 104.0% | — |
| 16337 | 2 | 3'-UTR | 18.3% | 81.7% |
| 16338 | 3 | 3'-UTR | 41.2% | 58.8% |
| 16339 | 4 | 3'-UTR | 23.5% | 76.5% |
| 16340 | 5 | stop | 29.8% | 70.2% |
| 16341 | 6 | stop | 22.5% | 77.5% |
| 16342 | 7 | stop | 20.6% | 79.4% |
| 16343 | 8 | coding | 35.8% | 64.2% |
| 16344 | 9 | coding | 15.3% | 84.7% |
| 16345 | 10 | coding | 25.2% | 74.8% |
| 16346 | 11 | coding | 40.6% | 59.4% |
| 16347 | 12 | AUG | 21.4% | 78.6% |

Example 3

Dose response of chimeric (2'-deoxy) gapped antisense phosphorothioate oligonucleotide effects on human TACE mRNA levels ISIS 16337 (SEQ ID NO. 2) was chosen for further studies including dose response assays. For dose response, cells were treated as described in Example 2, except the concentration of oligonucleotide was varied. LIPOFECTIN® was added at a 10 μg/ml. The control included LIPOFECTIN® at a concentration of 10 μg/ml. In HUVEC cells, the IC50 was approximately 50 nM, while in neoHK cells, the IC50 was 150 nM. Control oligonucleotides, targeting human TNF-α or mouse CD18, had no effect on TACE MRNA levels.

Example 4

Time course of chimeric (2'-deoxy) gapped antisense phosphorothioate oligonucleotide effects on human TACE mRNA levels To investigate the role of TACE in cell processes, the effect of TACE oligonucleotides on mRNA and protein levels over time was determined. Jurkat and THP-1 cells were treated with 20 μM oligonucleotide as described in Example 2. Results are shown in Table 4.

TABLE 4

Inhibition of Human TACE mRNA and protein Expression in Jurkat Cells by Chimeric (2'-deoxy) Gapped Oligonucleotides

| ISIS No: | SEQ ID NO: | GENE TARGET REGION | TIME (hours) | % mRNA EXPRESSION | % protein EXPRESSION |
|---|---|---|---|---|---|
| basal | — | — | — | 100.0% | 100.0% |
| 16337 | 2 | 3'-UTR | 24 | 53.5% | 22.3% |
| " | " | " | 48 | 30.1% | 29.0% |
| " | " | " | 72 | 41.7% | 36.9% |

TABLE 4-continued

Inhibition of Human TACE mRNA and protein Expression in Jurkat Cells by Chimeric (2'-deoxy) Gapped Oligonucleotides

| ISIS No: | SEQ ID NO: | GENE TARGET REGION | TIME (hours) | % mRNA EXPRESSION | % protein EXPRESSION |
|---|---|---|---|---|---|
| 17965 | 13 | control | 24 | 104.4% | 95.9% |
| " | " | " | 48 | 104.8% | 101.2% |
| " | " | " | 72 | 95.8% | 92.3% |

ISIS 16337 (SEQ ID NO. 2) reduced both TACE mRNA and protein levels at 24, 48, and 72 hours after transfection in Jurkat cells. Treatment with the TACE antisense oligonucleotide resulted in greater than 75% inhibition of protein expression, which remained suppressed for up to 72 hours. TACE MRNA levels were reduced by about 70% at 48 hours and remained suppressed at 72 hours. The 3 base mismatch control oligonucleotide, ISIS 17965 (SEQ ID NO. 13), had no effect on either TACE mRNA or protein levels. Similar results were seen in THP-1 cells.

Example 5

Effect of TACE antisense oligonucleotides on L-selectin shedding

The role of TACE in promoting PMA-induced L-selectin shedding was investigated in Jurkat cells. Jurkat cells were electroporated with 20 μM of oligonucleotide as described in Example 2. 6.4×10⁵ cells were electroporated in OPTI-MEM™ I media (Life Technologies) containing 1% FCS (Life Technologies) at room temperature with an electric field strength of 750 V/cm. 24 hours after oligonucleotide treatment, L-selectin shedding was induced with 100 nM PMA (Calbiochem, ) for 5 minutes at 37° C. L-selectin cell surface expression was analyzed by flow cytometry using a FACScan as described in Example 2.

Results are shown in Table 5.

TABLE 5

Inhibition of L-selectin Shedding in Jurkat Cells by Chimeric (2'-deoxy) Gapped TACE Antisense Oligonucleotides

| ISIS No: | SEQ ID NO: | GENE TARGET REGION | TIME (hours) | % L-selectin expression | % L-selectin inhibition |
|---|---|---|---|---|---|
| basal | — | — | — | 100.0% | — |
| E.P.[1] | — | — | 24 | 18.3% | 81.7% |
| " | " | " | 48 | 33.6% | 66.4% |
| " | " | " | 72 | 31.0% | 69.0% |
| 16337 | 2 | 3'-UTR | 24 | 95.6% | 4.4% |
| " | " | " | 48 | 96.0% | 4.0% |
| " | " | " | 72 | 97.4% | 2.6% |

TABLE 5-continued

Inhibition of L-selectin Shedding in Jurkat Cells by Chimeric (2'-deoxy) Gapped TACE Antisense Oligonucleotides

| ISIS No: | SEQ ID NO: | GENE TARGET REGION | TIME (hours) | % L-selectin expression | % L-selectin inhibition |
|---|---|---|---|---|---|
| 17965 | 13 | control | 24 | 17.1% | 82.9% |
| " | " | " | 48 | 32.2% | 67.8% |
| " | " | " | 72 | 35.9% | 64.1% |

[1]E.P. refers to cells electroporated without oligonucleotide

In cells in which TACE expression had been reduced by the TACE antisense oligonucleotide, treatment with PMA resulted in a dramatic decrease in L-selectin shedding. In contrast, in cells that were treated with the control or the TNF-α antisense oligonucleotide, PMA still induced L-selectin shedding. ISIS 16337 (SEQ ID NO. 2) did not alter the surface expression of other adhesion molecules including CD3, CD45, LFA-1 or α4 integrin, either in the presence or absence of PMA induction.

Example 6

Effect of TACE antisense oligonucleotides on TNF-α processing

The role of TACE in promoting PMA-stimulated TNF-α processing and secretion was investigated in THP-1 cells. THP-1 cells were electroporated with 20 μM of oligonucleotide as described in Example 5. 24 hours after oligonucleotide treatment, cells were treated with 100 nM PMA (Calbiochem-Novabiochem Corp., San Diego, Calif.) for 6 hours. Following PMA treatment, TNF-α release was then triggered with 1 μg/ml of lipopolysaccharide (LPS) overnight at 37° C. The supernatant was harvested and assayed for TNF-α using the Cytoscreen Immunoassay Kit (Biosource International, Camarillo, Calif.) according to the manufacturer's instructions.

ISIS 14834 (SEQ ID NO: 14) is an fully phosphorothioated oligodeoxynucleotide targeted to TNF-α and was used as a positive control.

Results are shown in Table 6.

TABLE 6

Inhibition of TNF-α Processing in THP-1 Cells by Chimeric (2'-deoxy) Gapped TACE Antisense Oligonucleotides

| ISIS No: | SEQ ID NO: | GENE TARGET REGION | % TNF-α secretion | % TNF-α inhibition |
|---|---|---|---|---|
| basal | — | — | 100.0% | — |
| 14834 | 14 | TNF-α | 38.2% | 61.8% |
| 16337 | 2 | 3'-UTR | 41.6% | 58.4% |
| 17965 | 13 | control | 107.7% | — |

Cells treated with the TACE antisense oligonucleotide, ISIS 16337 (SEQ ID NO. 2), decreased the quantity of soluble TNF-α produced. The level of reduction was similar to a TNF-α specific antisense oligonucleotide, ISIS 14834 (SEQ ID NO. 18). The mismatch control oligonucleotide had no effect on TNF-α secretion.

What is claimed is:

1. An antisense compound 8 to 30 nucleobases in length targeted to nucleotides 2911 through 2930, nucleotides 2641 through 2660 or nucleotides 2681 through 2700 of a 3'-untranslated region, nucleotides 2770 through 2603 of a stop codon region, nucleotides 131 through 150, nucleotides 2471 through 2490 or nucleotides 2531 through 2570 of a coding region, or nucleotides 114 through 133 of an AUG codon region of human TNF-α converting enzyme SEQ ID NO: 1, wherein said antisense compound inhibits expression of human TNF-α converting enzyme.

2. The antisense compound of claim 1 which is an antisense oligonucleotide.

3. The antisense compound of claim 2 which comprises at least one modified internucleoside linkage.

4. The antisense compound of claim 3 wherein the modified internucleoside linkage is a phosphorothioate linkage.

5. The antisense compound of claim 2 which comprises at least one modified sugar moiety.

6. The antisense compound of claim 5 wherein the modified sugar moiety is a 2'-O-methoxyethyl sugar moiety.

7. The antisense compound of claim 2 which comprises at least one modified nucleobase.

8. The antisense compound of claim 7 wherein the modified nucleobase is a 5-methylcytosine.

9. The antisense compound of claim 2 which is a chimeric oligonucleotide.

10. A composition comprising the antisense compound of claim 1 and a pharmaceutically acceptable carrier or diluent.

11. The composition of claim 10 further comprising a colloidal dispersion system.

12. A method of modulating processing of TNF-α, in human cells or tissue, from its membrane bound form to its secreted form comprising contacting said cells or tissue in vitro with the antisense compound of claim 1 so that expression of TNF-α converting enzyme is inhibited and processing of TNF-α is inhibited.

13. A method of modulating the expression of TNF-α converting enzyme in human cells or tissues comprising contacting said cells or tissue in vitro with the antisense compound of claim 1 so that expression of said TNF-α converting enzyme is inhibited.

14. An antisense compound up to 30 nucleobases in length comprising at least an 8-nucleobase portion of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12 which inhibits the expression of human TNF-α converting enzyme.

* * * * *

UNITED STATES PATENT AND TRADEMARK OFFICE
CERTIFICATE OF CORRECTION

PATENT NO. : 6,180,403 B1
DATED : January 30, 2001
INVENTOR(S) : Flournoy et al.

It is certified that error appears in the above-identified patent and that said Letters Patent is hereby corrected as shown below:

<u>Column 13,</u>
Line 4, please delete "enetration" and insert -- penetration --.

<u>Column 39, claim 1,</u>
Line 58, please delete "2770" and insert -- 2570 --.

Signed and Sealed this

Twenty-ninth Day of January, 2002

Attest:

*Attesting Officer*

JAMES E. ROGAN
*Director of the United States Patent and Trademark Office*